United States Patent [19]

Lawrence, Jr. et al.

[11] 4,113,771

[45] Sep. 12, 1978

[54] PROCESS FOR THE PURIFICATION OF CITRIC ACID

[75] Inventors: Walter W. Lawrence, Jr., Tom W. McKay, Karl E. Wiegand, all of Baton Rouge, La.

[73] Assignee: Ethyl Corporation, Richmond, Va.

[21] Appl. No.: 807,738

[22] Filed: Jun. 17, 1977

Related U.S. Application Data

[60] Division of Ser. No. 325,174, Jan. 19, 1973, which is a continuation-in-part of Ser. No. 131,885, Apr. 7, 1971, Pat. No. 3,770,796.

[51] Int. Cl.$^2$ .................... C07C 59/16; C07C 101/20
[52] U.S. Cl. ..................................... 562/568; 562/580
[58] Field of Search ......................... 260/534 E, 535 P

[56] References Cited

U.S. PATENT DOCUMENTS

| 3,769,337 | 10/1973 | Wiegand | 260/535 P |
| 3,769,338 | 10/1973 | Daganl et al. | 260/535 P |
| 3,917,685 | 11/1975 | Bergeron | 260/535 P |

*Primary Examiner*—Paul J. Killos

[57] ABSTRACT

It is disclosed that citric acid and salts thereof are readily produced by reacting acetone dicarboxyl ions, cyanide ions and alkali metal ions to produce an intermediate system which is subsequently reacted in an excess caustic system to form a salt of citric acid and that the salt is readily recovered by precipitation from the excess caustic system under proper conditions of concentration and temperature without requiring the formation of calcium salts. The recovered salt may be used directly or may be subjected to additional purification or may be converted to citric acid or other salts thereof by treatment with an acidification system such as sulfuric acid.

3 Claims, No Drawings

PROCESS FOR THE PURIFICATION OF CITRIC ACID

REFERENCE TO RELATED APPLICATION

This is a division of application Ser. No. 325,174, filed Jan. 19, 1973, now pending, which in turn is a division of application Ser. No. 131,885, filed Apr. 7, 1971, now U.S. Pat. No. 3,770,796.

BACKGROUND OF THE INVENTION

1. Field of the Invention

The invention relates to the preparation of citric acid and of its anhydrous or hydrous salts.

2. Description of the Prior Art

In the past, citric acid and its derivatives have been obtained primarily from natural sources such as citrus fruit and production via mycological or fermentation processes. The recovery of citric acid from natural sources is disclosed in U.S. Pat. Nos. 2,027,264; 2,193,904 and 2,396,115. The production of citric acid by mycological processes is disclosed in U.S. Pat. Nos. 2,353,771; 2,739,923; 2,883,329 and 3,335,067.

Citric acid and derivatives such as the alkali metal salts thereof are useful in different ways as exemplified by the following patents. As a plasticizer, U.S. Pat. No. 2,409,703. As a bleaching agent, U.S. Pat. No. 2,529,831. As a food antioxidant, U.S. Pat. No. 2,563,855. As a detergent component, U.S. Pat. No. 2,765,280. Another reference providing useful information in connection with citric acid is Braverman, J. B. S., "Citrus Products", Interscience, New York, 1949, page 333–348.

The production of acetone dicarboxylic acid is discussed by H. Schulte and A. Yarsin, Ber., Vol. 89, page 714 (1956).

SUMMARY OF THE INVENTION

The present invention relates to a plural step process for producing citric acid or its alkali metal salts. The process reacts acetone dicarboxyl ions, cyanide ions and alkali metal ions in the proportions of about 1 mol equivalent cyanide ions ($CN^{\ominus}$) and from about 1.5 to about 2.0 alkali metal atom or ion equivalents ($Me^{\oplus}$) per mol equivalent acetone dicarboxyl ions

for from about 0.1 to about 72 hours, at a temperature of from about 0° to about 100° C.

The system from the preceding reaction is then combined with caustic to provide a resulting caustic solution containing from about 5 to about 40 percent by weight of caustic. The caustic solution is reacted for from about 0.25 to about 8 hours at a temperature of from about −10° to about 180° C. During this time caustic is added if necessary to maintain a desired caustic concentration in the solution as the reaction consumes caustic from the solution producing trisodium citrate dihydrate which may precipitate.

The trisodium citrate dihydrate thus produced readily precipitates and is recovered by separation operations such as decentation, filtration, centrifuging, and the like. The precipitation is enhanced at temperatures below about 50° C.

When the cyanide, alkali metal and acetone dicarboxyl ions are combined in the proportions indicated, reaction is virtually instantaneous at the temperatures indicated.

Preferably feed materials used at the various steps of the process involve compounds of a single alkali metal, obtained by feed of a solution of the hydroxide, oxide, carbonate, or bicarbonate. A preferred source of cyanide ion is a cyanide of the same alkali metal as that of the caustic providing some of the alkali metal needed for the reaction as well as the cyanide. Another source of cyanide is HCN. Acetone dicarboxylic acid may be supplied in the form of its alkali salt as well as the acid.

It will be recognized that the acetone dicarboxyl ions, the alkali metal atoms, the cyanide ions and the protons involved may be derived from any combination consistent with the principle of electroneutrality such as hydrogen cyanide, alkali hydroxide or oxide, acetone dicarboxylic acid or its alkali salts, and/or alkali metal cyanide such that the number of cyanide radicals is sufficient to convert a major portion of the acetone dicarboxyl ions to a corresponding cyanohydrin resulting in a mildly acidic solution. Thus, it is immaterial whether the acidic protons are derived from hydrogen cyanide or acetone dicarboxylic acid and whether the alkali metal atoms are supplied externally as alkali hydroxide, oxide or carbonate or derived from alkali cyanide or alkali acetone dicarboxylate. Alternately, although typically less desirable, the proper acidity may be derived from an "externally" derived acid, typically a mineral acid such as sulfuric, hydrochloric, phosphoric, fluosilicic, and nitric, as well as an organic acid such as acetic, formic, oxalic, succinic and the like. With such "external acids" the purification stages provide for the separation of the resulting salts of these acids from the system. Finally, acid forms of ion exchange substances such as ion exchange resins or organosoluble-aqueous insoluble acids may be used to supply acidity while being easily separable upon consumption via filtration, fixed bed or fluidized bed, decantation or liquid phase separation.

Preferred caustic is sodium hydroxide and a preferred source of cyanide is sodium cyanide. Useful proportions of the reactants in the initial phase are about 1 "mol equivalent" ions of cyanide ($CN^{\ominus}$) and from about 1.5 to about 2.0 alkali metal "atomic equivalents" ($Me^{\oplus}$) per mol equivalent of acetone dicarboxyl ions, acid or alkali metal salt thereof. The term "about" with respect to cyanide equivalents (relative to the alkali metal and acetone dicarboxyl ions) generally is satisified by a range of from 0.9 to 1 to 1.1 to 1. A narrower range for cyanide equivalents is 0.95 to 1 to 1.1 to 1 and for alkali metal equivalents relative to acetone dicarboxyl ions is from about 1.6 to 1 to about 1.9 to 1. Preferred ratios are equivalent to one cyanide ion ($CN^{\ominus}$) per 1.75 atoms of sodium ($Na^{\oplus}$) and per divalent acetone dicarboxyl ion

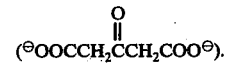

As is apparent from the previous discussion, these proportions may be written in ionic form as

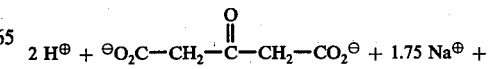

-continued

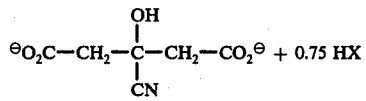

where $X^\ominus = OH^\ominus$, $\frac{1}{2} CO_3^\ominus$, $\frac{1}{2} O^\ominus$, $HCO_3^\ominus$ and the like and are, as ions, independent of their initial particular combination once they are combined in solution.

An important aspect of the process of the present invention is that in the first phase reacting step there be insufficient caustic present to provide free caustic in the system or even to provide as much as about two atoms of alkali metal per molecule of acetone dicarboxylic acid. Preferably, there is a slight deficiency of alkali metal atoms relative to that required to provide two alkali metal atoms per molecule of acetone dicarboxylic acid and per cyanide ion. Such a slight deficiency is represented in the 1.9:1 ratio.

The temperature of the foregoing reaction is suitably conducted at from about 0° to about 100° C., preferably from about 25° to about 65° C., typically at about 50° C.

The first step of the process has characteristics of an ionic type of reaction which progresses with great rapidity. Reaction times as short as about one minute are practical in well agitated systems with times up to several days being useful. A preferred reaction time is two hours at about 50° C. Preferably, the reactants are fed more or less continuously to provide the approximate molar-ionic proportions indicated. Alternately, under appropriate circumstances, the reactants may be added to the system individually in sequence in a batch-wise or semi-continuous operation; however, caution is usually required in this type of addition to minimize losses and attendant poor yields.

The first phase reacting step is preferably performed at a pH of from about 2 to about 10, a more preferred pH being from about 4 to about 6. A typical pH is 5.5.

It is desired to avoid a large excess of $CN^\ominus$ ions at the end of the first phase reaction to avoid excessive losses of unreacted cyanide and by-product reactions. It is desired to avoid excess caustic at this stage because of the increased tendency to side reactions involving the caustic and poor yields with ph more basic than about 7.5.

The following typical reactions appear to be involved up to this point. Other alkali metal compounds and HCN may be substituted in appropriate proportions as sources to yield the proper quantities or ratios of the ions specified in the previous discussion.

Ionizations:

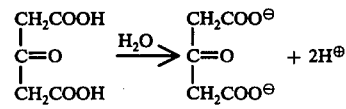

Overall:

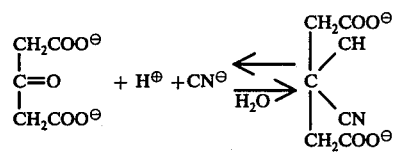

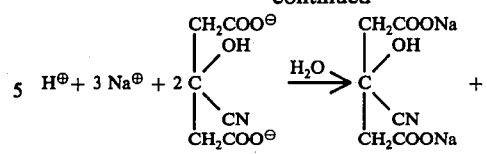

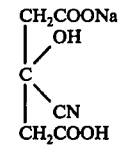

At this point it is possible to reversibly remove the incipient carboxyl functionality derived from the cyanide group, i.e. the main reaction independent of pH is

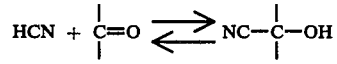

If the pH is too high HCN is eliminated from the cyanohydrin. Thus, whereas simple organo cyanides are hydrolyzable with either acidic or basic catalysts, in the case of cyanohydrins acidic hydrolysis is the method of choice. Typically, it is necessary to heat a cyanohydrin with concentrated acid in order to achieve a practical hydrolysis rate. A unique feature of our discovery is that the cyanohydrin of acetone dicarboxylic acid may be hydrolyzed with limited acidity and that acetone dicarboxylic acid or its cyanohydrin are sufficiently strong acids themselves to catalyze the hydrolysis to the amide.

The hydrolysis of the cyanohydrin to amide is represented by the equation for the sodium hydrogen cyanohydrin:

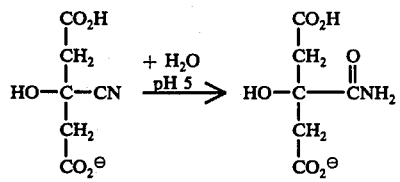

The hydrolysis of the cyanohydrin to the amide is a slow reaction, accounting for most of the time required in the first phase (A) process step.

Although the first phase (A) process step can be performed in more than a single stage using similar conditions in the various stages, it usually is preferred to operate a staged reactor system with somewhat different conditions in the various stages. Generally, this implies temperature differences of at least about 5° C. between each stage of a plural stage reactor system used for the first phase reaction A.

Thus, in a preferred arrangement of the present process, the first step A is conducted in at least two stages one of which is at a temperature of from about 0° C. to about 60° C. for about 5 seconds to about 15 minutes with a pH of from about 4 to about 6 while another is at a temperature of from about 25 to about 75° C. and which is at least 5° C. different from the first stage, for about 0.1 to about 72 hours. Preferably, the second stage is at a temperature higher than that of the first stage.

Although we do not wish to be restricted by discussion of mechanism, it appears that such a second stage provides a way to separate at least a part of the instantaneous cyanohydrin formation reaction previously shown from the hydrolysis whereby the cyanohydrin is converted to the amide.

In the reaction step performed in the presence of the strong free caustic, it appears that the amide hydolyses to produce the hydroxy tricarboxyl ion which precipitates out as the trialkali metal hydroxyl tricarboxylic sodium salt, usually in the dihydrate form.

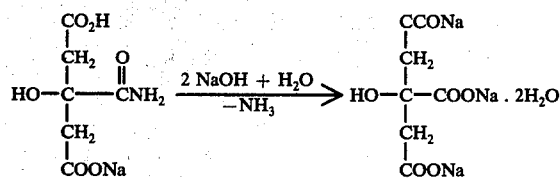

Where desired, the amide solution prior to the final hydrolysis may be subjected to purification and recovery operations such as distillation, filtration, degassing under vacuum, absorption or adsorption using particulate materials such as activated alumina, silica gel, activated animal charcoal, vegetable charcoal, solvent extraction as with organic solvents such as toluene, carbon tetrachloride and the like.

The final hydrolysis reaction, step "B" of the process uses an excess caustic condition which preferably is realized by adding enough caustic to the system to produce and maintain an aqueous system where the solution contains from about 5 to about 40 percent by weight of caustic. This concentration is expressed on a basis of the resulting fully reacted solution itself which contains water, dissolved caustic and a saturation amount of dissolved [Na$_3$ Citrate 2 H$_2$O]. Any precipitated Na$_3$ Citrate 2 H$_2$O present is not included in determining this proportion. A preferred narrower range for caustic concentration in the solution is from about 10 to about 30 percent caustic, with 15-25 percent more preferred. A typical figure is about 20 percent caustic. Under such an excess caustic condition, intermediates from the first reaction react further to produce trisodium citrate dihydrate which has low solubility in the caustic solution under the caustic concentration conditions described at temperatures from about −10° C. to about 50° C., preferably from about 5 to about 30° C., typically about 15 to 20° C., and thereby precipitates readily. Times for the reaction B are from about 0.25 to about 8 hours. A preferred narrower range is from about 0.5 to about 6 hours.

Although the caustic reaction proceeds at the precipitation temperatures indicated and the equilibrium can be enhanced by the precipitation, it frequently is preferred to initially operate in a first stage of this step at the higher temperatures previously indicated; viz, from about 50° to about 180° C. for at least a part of the 0.25 to 8 hour time specified, and then operate at a lower temperature in the range of from about minus 10° to about 50° C. in a second stage of the step for the balance of the time. Alternately, this lower temperature operation if used may be viewed as being conducted wholly or in part within the subsequently described recovery step C of the process.

The trisodium citrate dihydrate precipitate that results is readily removed from the mother liquor by conventional separation procedures such as decantation, filtration, centrifugation, and the like, individually and in various combinations. All or part of the resulting mother liquor which contains the excess caustic and residual Na$_3$ Citrate 2 H$_2$O is recycled to either or both of the first or second step of the process as part of the alkali metal or caustic requirements for either or both points. In general, a recycle to the excess caustic operative step is preferred to minimize decomposition of the contained Na$_3$ Citrate 2 H$_2$O.

The recovered trisodium citrate dihydrate is typically washed one or more times with water or caustic solution or lower alcohols such as methanol, ethanol or isopropanol to remove residual mother liquor providing caustic and citrate containing washings which are added to the mother liquor for recycle or are recycled separately to either or both of the first or second steps or otherwise disposed of. The washed trisodium citrate dihydrate is dried preferably to remove surface or occluded moisture providing an easily handled particulate solid product of trisodium citrate dihydrate.

In most cases the product thus obtained is directly usable without further purification. Additional purification is practical where desirable to provide an even highr purity. For example, the trisodium citrate dihydrate may be dissolved in water, the resulting solution being subjected to distillation, filtration, degassing, adsorption or absorption and other purification as previously described for the cyanohydrin or amide solution. The purified solution resulting is then treated with caustic to provide the about 5 to about 40 percent excess caustic condition previously described as useful for causing reprecipitation of the trisodium citrate dihydrate which is recovered from its mother liquor as previously described for the freshly produced sodium citrate. The mother liquor obtained at this point typically contains all or at least part of the caustic feed required for the first and second steps of the process and is conveniently fed to either or both as desired, preferably to the latter.

Recrystallization may be performed second and additional times for additional purity enhancement. In the event that recrystallization is used, normally the drying step for the NA$_3$ citrate.2H$_2$O is performed only once, after the final crystallization of the sequence, being omitted in intermediate phases except in circumstances where shipment, prolonged storage or other special handling of an intermediate product makes such desirable.

Acetone dicarboxylic acid starting material used in the process of the present invention is obtained from any suitable source. It may be purchased from commercial sources or produced directly. As an example of a way that acetone dicarboxylic acid may be produced, reference is had to H. Schulte, A. Yarsin, Ber. Vol. 89, page 714 (1956). In this process, acetone dicarboxylic acid is produced by first reacting malonic acid and thionyl chloride to produce malonyl chloride which is heated thiourea to liberate HCl producing 6-chloro-2-hydroxypyrone-3-carboxylic acid. The pyrone compound is then treated with water liberating additional HCl and carbon dioxide producing acetone dicarboxylic acid. The salt is obtained by reacting the acid and caustic.

The formation of a soluble intermediate compound by the reaction of acetone dicarboxylic acid, cyanide and alkali metal as discussed herein as well as the conversion thereof to the trisodium citrate is unexpected. It is believed that an intermediate compound is the cyanohydrin. The formation of this compound under near-neutral conditions (pH 4.0–6.0) is considered to be surprising because hydroxyl ions are on the same side of the equilibrium equation as the cyanohydrin. Seemingly, therefore, if one sought to produce the cyanohydrin intermediate, he would expect to use acidic conditions to favorably influence the equilibrium, and strongly acidic conditions at that. Thus, it is considered that the normal approach of one skilled in the art would be to expect to have to avoid hydrolysis of the cyanohydrin by avoiding neutral or weak conditions, particularly weakly acidic conditions such as a pH of 5.5.

The person skilled in the art also knows that acetone dicarboxylic acid has a tendency toward decarboxylation under strongly acidic or basic conditions. Thus, not only is the formation of the cyanohydrin unexpected, but one would not expect to be able to obtain conditions that could be used for the formation of the cyanohydrin without experiencing conditions that would convert one of the starting materials to something other than the cyanohydrin.

Certain aspects of the present process provide purification capability for citrate salts and citric acid produced in this and in other processes. Such acid or salt, if not in solution form, is combined with water to form an aqueous system which can be subjected to purification operations as hereinafter described following which the citrate is reprecipitated from a strong caustic solution as in the first precipitation of the foregoing. Sodium citrate is thus recovered producing a mother liquor which is recycled to the reprecipitation solution or to the initial preparation or to the precipitation solution. When this type of recycle of mother liquors is used with the present processing, the mother liquor from the first recovery operation preferably is fed to the reaction system of the acetone dicarboxylic acid, the cyanide and the alkali metal to provide at least a part of the alkali metal needed at that point.

Although water is a preferred solvent or diluent media for the present process in its entirety, other solvents or diluents may be used for all or parts of the process including crystallization or recrystallization and recycles of mother liquors.

Suitable other solvents are protic solvents such as lower alkanols and glycols having up to about six carbon atoms per molecule such as methanol, ethanol, ethylene glycol, diethylene glycol, mono-alkyl ethers of ethylene and diethylene glycol, and their mixtures with water.

Accordingly, the present application relates to a process for producing alkali metal salts of citric acid in at least two steps in which the first step involves forming a system of acetone dicarboxyl ions, cyanide ions and alkali metal ions. The proportions are about 1 mol equivalent cyanide ions and from about 1.5 to about 2.0 alkali metal atom equivalents per mol equivalent of acetone dicarboxyl ions. The system is reacted for from about 0.1 to about 72 hours, at a temperature of from about 0° to about 100° C. In the second step of the process, the system from the first step is reacted with caustic in a solution containing from about 5 to about 40 percent by weight caustic of an alkali metal such as sodium, potassium, or lithium for from about 0.25 to about 8 hours at a temperature from about −10° to about 180° C.

In a preferred aspect of the present process, at least a part of the cyanide ions is provided by feeding HCN.

In a preferred aspect of the process at least a part of the acetone dicarboxyl ions and alkali metal ions is provided by feeding an alkali metal acetone dicarboxylate.

In another preferred aspect of the present invention, at least a part of the acetone dicarboxyl ions is provided by feeding acetone dicarboxylic acid.

In one preferred aspect of the present invention, the cyanide ions and part of the alkali metal ions reacted at Step A are provided by feeding alkali metal cyanide while part of the alkali metal is provided by feeding alkali metal hydroxide, oxide or carbonate.

In a preferred aspect of the present invention, the alkali metal is sodium and part of the alkali metal is provided by feeding sodium hydroxide or potassium hydroxide.

In a preferred aspect of the present invention, the second step feed of the reaction is an alkali metal hydroxide, oxide or carbonate, and preferably the alkali metal thereof is the same alkali metal as that whose ions are reacted in Step A.

In a preferred aspect of the present invention, the cyanide in at least part of the alkali metal reacted in Step A are provided by feeding alkali metal cyanide, particularly sodium cyanide or potassium cyanide.

Preferably the alkali metal cyanide is sodium cyanide and the caustic fed at Step B is sodium hydroxide.

A more preferred time for the first step of the present process from about 0.5 to about 4 hours with about 2 hours being typical.

A more preferred temperature for the first step of the present process is from about 25° to about 65° C. with about 50° C. being typical.

The atomic equivalents of alkali metal ($Na^+$) relative to the other reactants as specified is preferably from about 1.60 to 1 to about 1.90 to 1, typically about 1.75 to 1.

Preferably, the concentration of caustic of the solution of Step B is from about 10 to about 30 percent by weight, more preferably from about 15 to about 25 percent by weight.

In a preferred aspect of the present invention the time for the second step reaction of the process is from about 0.5 to about 6 hours. Typically, the reaction B is conducted in two phases with a first phase at a temperature from about 90° to about 100° C. and wherein the second phase of that step is at a temperature from about −10° to about 50° C.

The pH at Step A is from about 2 to about 10, preferably from about 4 to about 6, typically about 5.5.

In a preferred aspect, the present process produces alkali metal salts of citric acid by reacting sodium cyanide, sodium hydroxide and acetone dicarboxylic acid in molar proportions of from about 1:0.5:1 to about 1:1:1 for from about 0.1 to about 72 hours at a temperature of from about 0° to about 100° C. Following the reaction just specified, the resulting system is reacted with caustic in a solution containing from about 5 to about 40 percent by weight caustic of an alkali metal for from about 0.25 to about 8 hours at from about −10 to about 180° C.

In a preferred aspect the present invention relates to a process for producing alkali metal salts of citric acid by first forming a system of acetone dicarboxyl ions, cyanide ions and alkali metal ions in the proportions of about 1 mol equivalent cyanide ions and from about 1.5 to about 2.0 alkali metal atom equivalents per mol equivalent acetone dicarboxyl ions. The system thus formed is reacted for from about 5 seconds to about 15 minutes, at a temperature of from about 0° to about 60° C., and a pH from about 4 to about 6. Following this initial reaction step, the system that results is reacted at a temperature of from about 25° to about 70° C. and which is at least about 5° C. different from that of the first reaction for a period of time of from about 0.1 to about 72 hours. Subsequently, the system from the preceding step is reacted with caustic in a solution containing from about 5 to about 40 percent by weight caustic for from about 0.25 hours to about 8 hours at from about 50° to about 180° C. Trisodium citrate dihydrate is then recovered from the system resulting.

In a preferred aspect of the process of the preceding paragraph, a mother liquor is obtained in the recovery step and at least a part thereof is recycled to at least one of the preceding steps to provide at least a part of the alkali metal ions fed or present in said steps. Typically, at least a part of the mother liquor in the system is purged from the system to control the build-up contaminants in the system. Typically, at least a part of the mother liquor is recovered at C and at least a part thereof is recycled to Step B as at least a part of the caustic in the solution at Step B. In a preferred aspect of the process of the preceding paragraph, a terminal portion of at least about 5 minutes of the reaction with caustic in the from about 5 to about 40 percent solution is at a temperature of from about −10° to about 50° C.

Novel compositions produced in the process of the present invention are the cyanohydrin of acetone dicarboxylic acid and the mono and dialkali metal salts thereof.

Novel compositions produced in the process of the present invention are the amide of acetone dicarboxylic acid and the mono and dialkali metal salts thereof.

In one aspect of the present invention, there is provided a method for producing trialkali metal citrate salts from impure citric acid or alkali metal salts thereof in which there is formed an aqueous solution of the impure citric acid or its salt, the solution is combined with caustic to form a system containing the trialkali metal salt of citric acid and an aqueous solution containing from about 5 to about 40 percent by weight of caustic. The trialkali metal salt of citric acid is then recovered as a precipitate from the system thus formed. In a preferred aspect, a mother liquor is recovered in the course of the recovery of the trialkali metal salt of citric acid and at least a part of the mother liquor is recycled to provide at least a part of the caustic combined in the process.

In a preferred aspect the present invention relates to a process for producing alkali metal salts of citric acid by first forming a system of acetone dicarboxyl ions, cyanide ions and alkali metal ions in the proportions of about 1 mol equivalent cyanide ions and from about 1.5 to about 2.0 alkali metal atom equivalents per mol equivalent acetone dicarboxyl ions. The system thus formed is reacted for from about 0.1 to about 72 hours at a temperature of from about 0° to about 100° C. Following the preceding reaction, the resulting system is reacted with caustic in a solution containing from about 5 to about 40 percent by weight caustic, for from about 0.25 hour to about 8 hours at from about −10° to about 180° C. forming a precipitate of trisodium citrate dihydrate. The precipitate is separated producing a first mother liquor. The precipitate is combined with water to form a solution and the solution is then combined with caustic to form a system containing the trialkali metal salt of citric acid and an aqueous solution containing from about 5 to about 40 percent by weight of caustic. The trialkali metal salt of citric acid precipitates from said system and is recovered as a precipitate producing a second mother liquor. At least a part of at least one of the first and second mother liquors is recycled to at least one of the foregoing steps particularly the reacting with caustic step and the second combining step.

With reference now to the Figure, there is shown a block diagram of a process embodying the above described features of the present invention. Acetone dicarboxylic acid, plus a source of cyanide ions, and plus a source of alkali metal such as an alkali metal hydroxide, oxide or carbonate, is fed to the reacting step 10 in proportions of about 1 mol equivalent ions of cyanide ($CN^-$) and from about 1.5 to about 2.0 atomic equivalents of total alkali metal ions ($Me^+$) per mol of acetone dicarboxylic acid.

In preferred embodiments wherein the source of cyanide ions is sodium cyanide (NaCN) or HCN + NaOH provides not only the $CN^-$ but also one atomic equivalent of alkali metal ions ($ME^+$) as well, and the alkali metal of the hydroxide, oxide or carbonate is sodium, (NaOH, ½ $Na_2O$, ½ $Na_2CO_3$, $NaHCO_3$) the foregoing proportions are equivalent to feeding about 1 mol of sodium cyanide and from about 0.5 to about 1.0 mols of sodium hydroxide or bicarbonate or from about 0.25 to about 0.50 mols of sodium oxide or carbonate per mol of acetone dicarboxylic acid. Similar relationships apply with KCN and caustic potash compounds and for similar compounds of other alkali metals such as those of lithium.

Where sodium acetone dicarboxylate and HCN are fed it usually is preferred to obtain the desired slightly acidic pH by feeding an acidic reactant such as mineral acid, typically $H_2SO_4$, or HCl, or an acid form of an ion exchange resin, or citric acid.

If the feed materials contain large amounts of strong acid anions, such as halogens, or sulfate, or are sources thereof, it may be necessary to feed extra strong caustic to provide equivalent cations to maintain the slightly acidic pH.

A feed of water at the reaction 10 is indicated in the Figure; however, generally it is preferable to preform one or more aqueous solutions of one or more of the reactants, typically the alkali metal source material (NaOH), as distinguished from the cyanide source material and the cyanide plus alkali metal source material (NaCN), and to feed the preformed solution or solutions without the further complication of metering or controlling a separate water feed to the reaction 10. In a typical case all of the water required at 10 is supplied in an aqueous solution of alkali metal hydroxide, oxide or carbonate, typically such as aqueous solution contains a selected standard composition of from about 5 to about 25 wt. percent NaOH and is derived from either or both fresh caustic fed to the system or from a recycle caustic solution recovered from a subsequent step of the process.

Although caustic solutions containing from about 1 to about 50 percent by weight water are usable in the system at 10, solutions having 40 percent and more NaOH provide quite viscous systems while solutions more dilute than about 5 percent NaOH involve unduly low volumetric efficiency of process equipment. The most preferred caustic feed solutions accompanying solid NaCN and "dry" acetone dicarboxylic acid are NaOH solutions which contain from about 10 to about 12 weight percent NaOH in which case separate water feed to 10 ordinarily is not required.

The system at 10 is typically maintained at a temperature of 40° C. and at atmospheric pressure and is provided with vigorous agitation.

Once the system described in the foregoing is formed under the conditions recited, conversion to the citric acid salts requires a decided excess caustic condition brought about by feeding additional alkali metal hydroxide, oxide, carbonate or bicarbonate solution. Prior to this, however, it may be desired to perform a purification operation at 11 to remove contaminants. Typical contaminants include residual starting materials, undesired intermediates, color or odor bodies or their precursors and various gaseous impurities such as ammonia, hydrogen cyanide, $CO_2$, nitrogen, and the like. Typically, the gaseous impurities are removed by subjecting the system to a vacuum environment with the application of moderate heat at a temperature of from about 40° to about 105° C. Normally it is not necessary to remove large amounts of water at this point; however, in the event that it is desirable to remove water for adjusting the concentrations or pH of various solutions or for flexibility with respect to feed, recycle, etc. such is readily performed at this point.

Following the reaction at 10, with or without purification at 11, the amide system from reaction 10 is reacted further at 12 as described forming a precipitate of the trisodium salt of citric acid usually in a hydrated form. To this end, the system from reaction 10 is combined with caustic at 12.

Although the amide is readily soluble in the system at 10, the trisodium salt of citric acid is only slightly soluble in aqueous solution containing about 20 percent by weight caustic at temperatures of from about 60° to about 150° C. and even less soluble at temperatures from −10° to about 50° C. Thus, with the system at 12 being supplied with caustic solution typically having a concentration of about 30 percent by weight, one additional mol of caustic reacts with each mol of amide resulting in the maintenance in the environment at 12 of a caustic excess desirable to enhance precipitation of the trisodium salt of citric acid and the elimination of ammonia which may be recovered for conversion to HCN and thence to sodium cyanide useful for recycle to the feed to 10.

Following the reaction and precipitation of step 12, the precipitated trisodium salt of citric acid is separated from the mother liquor in product recovery 13. In general, any suitable conventional form of separation operation for the removal of a crystallized material from its mother liquor is suitably performed at 13, typically decantation, filtration centrifuging or the like. In general, in this step and in the process where there is no liberation of $CO_2$, it is desirable to minimize contacts with air which result in the absorption of $CO_2$. The generally preferred operation for recovery 13 is centrifuging which may be performed in either a batchwise or a continuous operation. Typically, the crystals are washed with pure NaOH solution, alcohol or water after the removal of the bulk of the mother liquor, the wash solution thus obtained usually being combined with the mother liquor removed at 13. Caustic and color may be removed from the crystals by one or two alcohol washes. The result of this is the production of a high purity hydrate salt of citric acid which is usable as such and which can be purified further if desired. Ordinarily, such additional purification is dispensed with except where food grade product is desired.

The mother liquor and wash water from the recovery 13 contain substantial amounts of caustic and residual amounts of the citric acid salt. Preferably, these materials are recovered by recycle of the material in whole or in part to either or both of the reaction step 10 or the reaction and precipitation step 12. To prevent the buildup to an inordinate level of circulating impurities within the system, it is usually desirable to purge a portion of the mother liquor from the system. Typically, the amount of purge varies from about one percent of the mother liquor to approximately 50 percent; however, in most instances it is unnecessary to purge more than from about 5 to about 10 percent of the mother liquor recycle stream. Because of the advantages of recovery and recycle of mother liquor, normally it is preferable to supply most or all of the caustic material introduced to the system thus far described to the reaction and precipitation step 12 or the wash at 13 eliminating entirely or reducing proportionately the amount of fresh caustic fed direct at reaction 10.

In the event it is desired to provide additional purification of the citrate salt produced at 13, salt from that operation is preferably dissolved in a solvent such as water at 14, following which it is subjected to purification at 15 involving operations such as those discussed in connection with purification 11 of the foregoing.

Following purification 15, or step 14 if purification is not performed at this point, the aqueous sodium citrate solution is recrystallized at 16 by supplying to it additional caustic in an amount sufficient to result in the production at that point of an aqueous solution containing about 30 percent caustic, a solution wherein the solubility of sodium citrate is extremely low as discussed in connection with reaction and precipitation step 12.

Precipitated sodium citrate from 16 is recovered from the mother liquor at 17 using operations similar to those discussed in connection with recovery 13. As the recovery 13, the trisodium citrate thus obtained is preferably washed with alcohol to remove residual amounts of mother liquor, providing a particulate trisodium product of high purity. Normally, it is desired to remove residual surface or occluded water or alcohol from the product trisodium citrate by a drying operation 18 which operation is typically performed at temperatures ranging from ordinary room temperature and atmospheric pressure up to super temperature and reduced pressures depending upon the circumstances involved. Generally speaking, temperatures higher than about 200° C. are desirably avoided at least for prolonged contact due to possible instability of the product under such conditions.

The mother liquor obtained from recovery 17 may be recycled to provide all or part of the caustic fed to the reaction and precipitation operation at 12 and/or the reaction at 10. In a typical sequence fresh caustic is supplied to a recrystallizing system at the precipitation step 16, and/or the wash of recovery 17, mother liquor from recovery 17 is fed to the reaction and precipitation at 12, and mother liquor from recovery 13 is supplied to reaction 10. The purge of mother liquor to prevent buildup of impurities within the system typically is accomplished by taking a side stream of about 5 percent of the mother liquor from recovery 13, the amount thereof being in accordance with the preceding discussion.

With the recycle of the various mother liquors as described, it is evident that in appropriate instances neither fresh caustic nor water is fed to either reaction 10 or 12 and that the water fed in the wash operations at 13 or 17 and the precipitation 16 constitute a major portion, if not all, of the makeup water fed to the entire system to replenish that removed in the mother liquor purge and in the purification operations 11 and 15 and via the purified product from 13 or 17.

It is evident from the foregoing that the entire process is well suited to continuous operation with feeds at the various steps being substantially continuous at the appropriate rates. It is evident, of course, that in appropriate circumstances that one or more of the reactions involved can be performed in a batchwise or semi-continuous manner or in several stages at similar or different temperatures and similar or different caustic concentrations. In instances where additional internal purification is required, the mother liquor from recovery 17 may be subjected to purification at 19 which typically is conducted along the lines indicated for purification steps 11 and 15.

The dried product obtained from 18 is typically a hydrate salt of trisodium citrate containing two molecules of water of hydration per molecule of salt. If desired, the drying step can be carried further to remove additional water; however, care is required in this instance to prevent undue destruction of the sodium citrate. Frequently, a vacuum removal is desired to minimize temperatures required for the removal.

Where it is desired to obtain citric acid per se, the product from 13 or 17, typically 17, is conveniently reacted in aqueous solution with a mineral acid such as sulfuric acid or hydrochloric acid in an amount necessary to produce citric acid or the mono- or disodium acid salts thereof, depending upon the specific product desired. Generally, it is convenient to recover the acid from a saturated or supersaturated solution of by-product salt such as sodium sulfate.

Alternately trisodium citrate may be converted to citric acid by contacting a solution with the acid form of a cation exchange resin which may be regenerated by the action of a mineral acid suh as sulfuric, hydrochloric, nitric, etc. The product so obtained is not contaminated with sodium salts and may be evaporated or crystallized directly.

There is obtained in this way citric acid of extremely high purity virtually devoid of characteristic natural impurities such as isocitric acid.

The purification system of the present invention is applicable directly to sodium citrate salts or citric acid derived from other sources. For example, trisodium citrate, disodium acid citrate, or sodium dihydrogen citrate or citric acid in hydrate form or otherwise, obtained from some other source is supplied to the melt stage 14 in substitution of all or part of the product from 13 as previously discussed. Following this then, the citric acid or salt solution produced at 14 is purified as described previously at 15 and the trisodium salt is precipitated at 16 and recovered at 17 as previously described.

Depending upon the form of purified product desired, the "other source" material recovered at 17 is delivered to acidification 20 or dryer 18 to provide respectively citric acid or its acid salts on the one hand or trisodium citrate (hydrate) on the other. Mother liquor obtained from product recovery 17 may be utilized by return to precipitation 16, usually with a purge stream or fraction thereof being withdrawn to prevent the buildup of impurities in the system. Alternately, the mother liquor from 17 can be purified at 19 before return to precipitation 16 or it may be delivered directly to some other system such as that of precipitation 12 of the production portion of the present process.

EXAMPLE I

500 Grams of acetone dicarboxylic acid, of purity of 98.6 percent equivalent to 493 g pure ADCA (3.374 mols) was reacted with 165.4 grams of sodium cyanide (3.374 mols) and 1,024 grams of a 10 percent by weight solution of sodium hydroxide in water (2.74 normal) and an additional 308 grams of water. The amount of NaOH contained in the solution was 101.2 grams (2.53 mols). The reaction was performed at 40° C.; the pH of the solution after combining the reactants was 5.5. The cyanohydrin formed initially was converted to the amide by heating and holding at 50° C. while stirring for 2 hours.

After filtering, the product from the foregoing reaction was then reacted with 322 grams of NaOH (8.05 mols) fed as a solid. The temperature of this reaction was held at 95° to 108° C. for 6 hours. Crystals began to form, were recovered from the mother liquor and washed with ethanol, and the crystals were analyzed in various ways. The sodium content was 23.4 wt. percent which compares with the theoretical for trisodium citrate.$2H_2O$ of 23.46. The nitrogen content was 6 parts per million which is quite low. Analysis by VPC showed 100 percent trisodium citrate.$2H_2O$. NMR and IR analyses provided spectra that compared essentially identically with authentic samples of trisodium citrate.$2H_2O$. Analysis for carbonate showed virtually no carbonate.

EXAMPLE II

A study of the solubility of trisodium citrate.$2H_2O$ in a 20 percent by weight of caustic solution was made. The study was conducted at 100° C. and at 15° C.. The data indicated that 40 grams of trisodium citrate.$2H_2O$ would dissolve at 100° C. in a solution containing 20 grams NaOH and 80 grams $H_2O$. At 15° C. in contrast the solubility of trisodium citrate.$2H_2O$ is only one half gram per 20 grams NaOH and 80 grams of $H_2O$. At 28° C. the solubility of trisodium citrate.$2H_2O$ in the 20 percent caustic solution is 15 grams per 100 grams of caustic solution.

EXAMPLE III

400 Grams of acetone dicarboxylic acid, of purity of 98.6 percent equivalent to 394.4 g pure ADCA (2.7 mols) was reacted with 132.3 grams of sodium cyanide (2.7 mols) and 972.5 grams of a 10 percent by weight solution of sodium hydroxide in water (2.77 normal) and an additional 97 grams of water. The amount of NaOH contained in the solution was 97.2 grams (2.43 mols). The reaction was performed at 50° C.. The cyanohydrin formed initially was converted to the amide by heating and holding at 75° C. while stirring for 1 hour.

After filtering, the product from the foregoing reaction was then reacted with 200 grams of NaOH (5.00 mols) fed as a solid. The temperature of this reaction was held at 90° to 100° C. for 6¼ hours. The mass was cooled to 10° C. and then allowed to come to room temperature and stand for 2 hours to provide time for crystal growth. Crystals began to form, were recovered from the mother liquor by filtration. The crystals were then redissolved by mixing with 450 ml of 20 percent NaOH solution per 100 grams of crystals and heating to 100° C.. The clear solution was filtered at 95° C. and allowed to cool to room temperature and stand overnight for crystal growth. The mixture was filtered at 15°-20° C. under vacuum. The crystals were washed with 2 volumes of ethanol, dried in a vacuum oven at 95° C. overnight. Yield 177 grams (0.6 mols) of 99 percent $Na_3$ citrate.$2H_2O$ containing less than 1 percent of $Na_2CO_3$ and NaOH impurities. The $Na_3$ citrate.$2H_2O$ purity was confirmed by NMR, IR, citrate precipitation with lead, VPC on the ester, and total organic acid assay. All were in agreement at the 99 percent purity figure.

EXAMPLE IV

The initial portions of Example I were repeated on a smaller scale (0.05 mol of acetone dicarboxylic acid) through the conversion to the amide. Conversions to the cyanohydrin and the amide were determined by NMR. About 80 percent of the starting acetone dicarboxylic acid was converted to amide.

EXAMPLE V

Example IV was repeated in two comparative tests. In one test the extra water was omitted. In the other test the amount of extra water was doubled.

In both tests the results indicated about 5–10 percent lower conversion to the amide with increased amounts of impurities.

EXAMPLE VI

Example IV was repeated with 8 percent increase in the amount of NaCN fed.

This increased the $Na^\ominus$ ions and increased the pH from 5.5 to 6.7. The impurities were increased and the conversion of the cyanohydrin to the amide was reduced.

EXAMPLE VII

The following data show the effect on the first reaction step "A" of varying the amount of NaOH in experiments similar to Example I but on a small scale. The conversions are based on NMR analysis.

| Mols of Starting Material | | | Percent Converted (By NMR Analysis) (40° C Reaction) | |
|---|---|---|---|---|
| Acetone Dicarboxylic Acid | NaOH | NaCN | To Cyanohydrin (10 Minutes Reaction Time) | To Amide (16 Hours Reaction Time) |
| 1 | 1.0 | 1.0 | 66 | 20 |
| 1 | 1.1 | 1.0 | 72 | 0 |
| 1 | 0.9 | 1.0 | 67 | 59 |

In conclusion, it is seen that the present invention provides a process for the synthesis of an alkali metal salt of citric acid which comprises reacting alkali metal cyanide, alkali metal hydroxide and alkali metal acetone dicarboxylate in solution in proportions equivalent to about 1 mol equivalent of cyanide ion and from about 1.5 to about 2.0 mol equivalents of alkali metal ion per mol equivalent of acetone dicarboxylate ion to form an amide intermediate and reacting said intermediate with alkali metal hydroxide in solution containing from about 5 to about 40 percent by weight of alkali metal hydroxide.

Patent No. 4,113,771
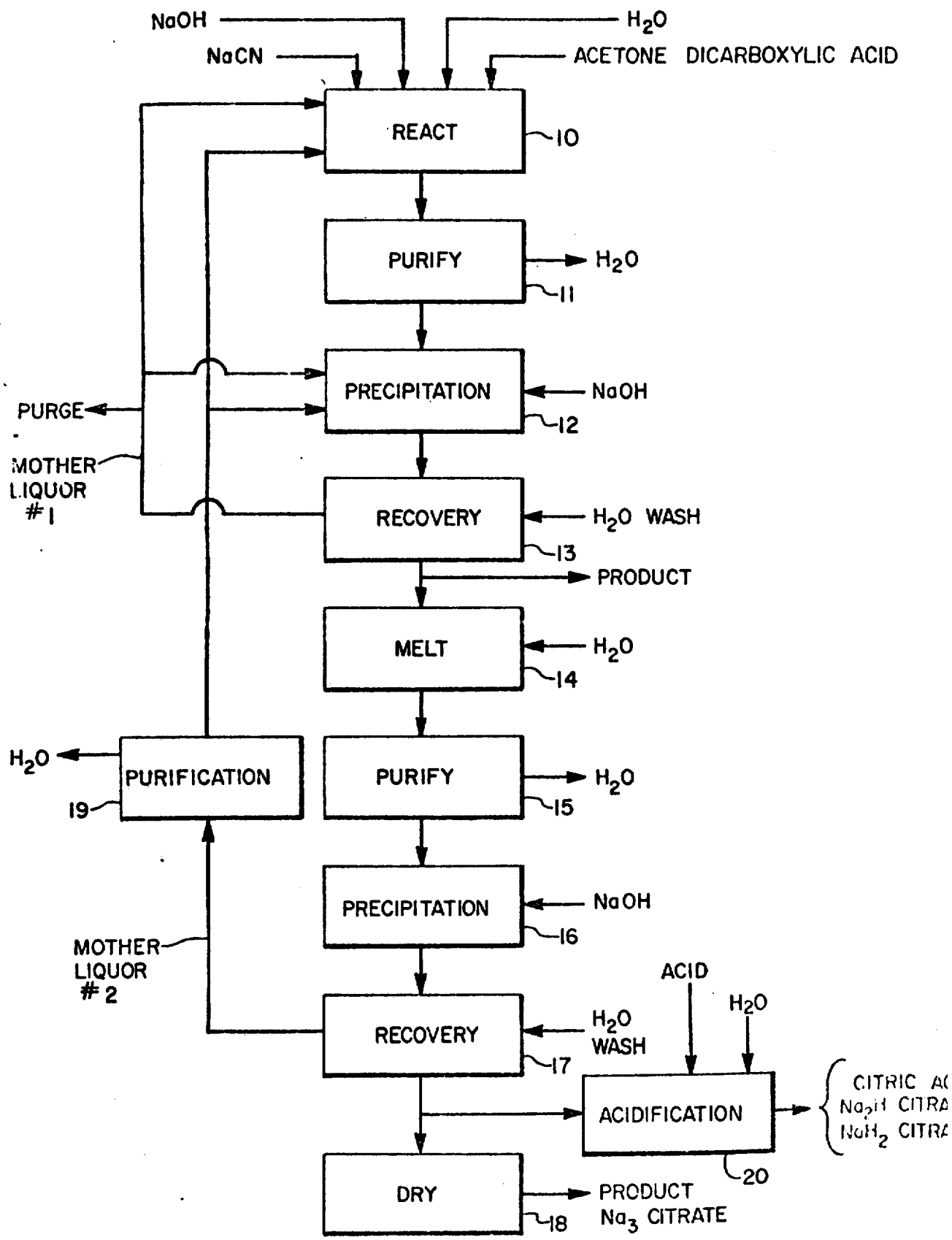

We claim:

1. The amide:

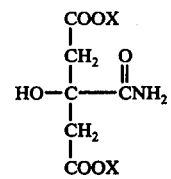

where X is H or alkali metal.

2. A method for producing purified trialkali metal citrate salts from impure citric acid or alkali metal salts thereof which comprises:
    A. forming an aqueous solution of the impure citric acid or its salt,
    B. combining said solution with caustic to form a system containing the trialkali metal salt of citric acid and an aqueous solution containing from about 5 to about 40 percent by weight of caustic, and
    C. recovering the trialkali metal salt of citric acid as a precipitate from the system formed at Step B.

3. The process of claim 2 wherein a mother liquor is recovered at C and at least a part thereof is recycled to Step B as at least a part of the caustic combined at Step B.

* * * * *

UNITED STATES PATENT AND TRADEMARK OFFICE
CERTIFICATE OF CORRECTION

PATENT NO. : 4,113,771
DATED : September 12, 1978
INVENTOR(S) : Walter W. Lawrence, Jr.; Tom W. McKay; and Karl E. Wiegand It is certified that error appears in the above-identified patent and that said Letters Patent are hereby corrected as shown below:

Cover Page in Item [56], "Daganl et al" should read -- Dagani et al --; Column 3, line 46, "ph" should read -- pH --; Column 3, line 64, "C$\begin{smallmatrix}CH\\CN\end{smallmatrix}$" should read -- C$\begin{smallmatrix}OH\\CN\end{smallmatrix}$ --; Column 5, line 15, "CCONa" should read -- COONa --; Column 10, line 8, "iis" should read -- is --; Column 10, line 23, "NaOH provides" should read -- NaOH which provides --; Column 10, line 45, "feeed" should read -- feed --; Column 10, line 56, "as" should read -- an --; Column 12, line 14, "mother liquor to" should read -- mother liquor up to --; Column 12, line 14, "trisodium product" should read -- trisodium citrate product --; Column 15, line 41, "Na$^-$" should read -- Na$^+$ --.

The attached sheet of drawing should appear as the sole sheet of drawing in the above-identified patent.

Signed and Sealed this

Tenth Day of June 1980

[SEAL]

Attest:

SIDNEY A. DIAMOND

Attesting Officer

Commissioner of Patents and Trademarks